(12) United States Patent
Becklund et al.

(10) Patent No.: US 12,172,022 B2
(45) Date of Patent: Dec. 24, 2024

(54) IMPLANTABLE MEDICAL DEVICE WITH RELATIVE MOTION CONTROL

(71) Applicant: CARDIAC PACEMAKERS, INC., St. Paul, MN (US)

(72) Inventors: Joel Becklund, Roseville, MN (US); James Michael English, Cahir (IE); Benjamin J. Haasl, Forest Lake, MN (US); Moira B. Sweeney, St. Paul, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 668 days.

(21) Appl. No.: 17/400,739

(22) Filed: Aug. 12, 2021

(65) Prior Publication Data
US 2022/0047876 A1 Feb. 17, 2022

Related U.S. Application Data

(60) Provisional application No. 63/065,277, filed on Aug. 13, 2020.

(51) Int. Cl.
*A61N 1/375* (2006.01)
*H05K 1/02* (2006.01)
*H05K 3/28* (2006.01)

(52) U.S. Cl.
CPC ....... *A61N 1/37512* (2017.08); *A61N 1/3758* (2013.01); *H05K 1/0271* (2013.01);
(Continued)

(58) Field of Classification Search
CPC .......................... A61N 1/37512; A61N 1/3758
(Continued)

(56) References Cited

U.S. PATENT DOCUMENTS 4,314,562 A 2/1982 Ware
5,876,424 A 3/1999 O'phelan et al.
(Continued)

FOREIGN PATENT DOCUMENTS

EP 2934670 B1 1/2018
WO 2012036944 A1 3/2012

OTHER PUBLICATIONS

Henkel, Presentation, Macromelt Molding, 35 pages, https://www.ellsworth.com/globalassets/literature-library/manufacturer/henkel-loctite/henkel-presentation-technolmelt-formerly-branded-as-macromelt-molding.pdf Accessed Mar. 2, 2020.
(Continued)

*Primary Examiner* — Nadia A Mahmood
(74) *Attorney, Agent, or Firm* — Seager, Tufte & Wickhem LLP

(57) ABSTRACT

An implantable medical device may include a plurality of electrical components connected to form operational circuitry, a canister shaped for housing the operational circuitry, and a dampening layer configured to reduce internal motion between the operational circuitry and at least one of a plurality of additional component within the canister, the dampening layer selectively disposed over the operational circuitry but not over the at least one additional component, the dampening layer providing electrical isolation to the operational circuitry, the dampening layer comprising a moldable material in direct contact with an inner surface of the canister. Methods of manufacturing such a medical device are also disclosed.

20 Claims, 19 Drawing Sheets

(52) U.S. Cl.
CPC ....... *H05K 3/28* (2013.01); *H05K 2201/2045* (2013.01); *H05K 2203/12* (2013.01)

(58) Field of Classification Search
USPC .......................................................... 607/36
See application file for complete search history.

(56) References Cited

U.S. PATENT DOCUMENTS

| | | |
|---|---|---|
| 7,194,309 B2 | 3/2007 | Ostroff et al. |
| 7,263,401 B2 | 8/2007 | Scott et al. |
| 7,769,457 B2 | 8/2010 | Fonte |
| 8,463,393 B2 | 6/2013 | Strother et al. |
| 9,713,725 B2 | 7/2017 | Bobgan et al. |
| 10,040,021 B2 | 8/2018 | Ries et al. |
| 2009/0034769 A1* | 2/2009 | Darley ............... A61N 1/36038 381/328 |
| 2015/0196867 A1 | 7/2015 | Ries et al. |
| 2015/0321013 A1 | 11/2015 | Smith et al. |
| 2018/0207427 A1 | 7/2018 | Webb et al. |

OTHER PUBLICATIONS

International Search Report and Written Opinion dated Nov. 19, 2021 for International Application No. PCT/US2021/045724.

\* cited by examiner

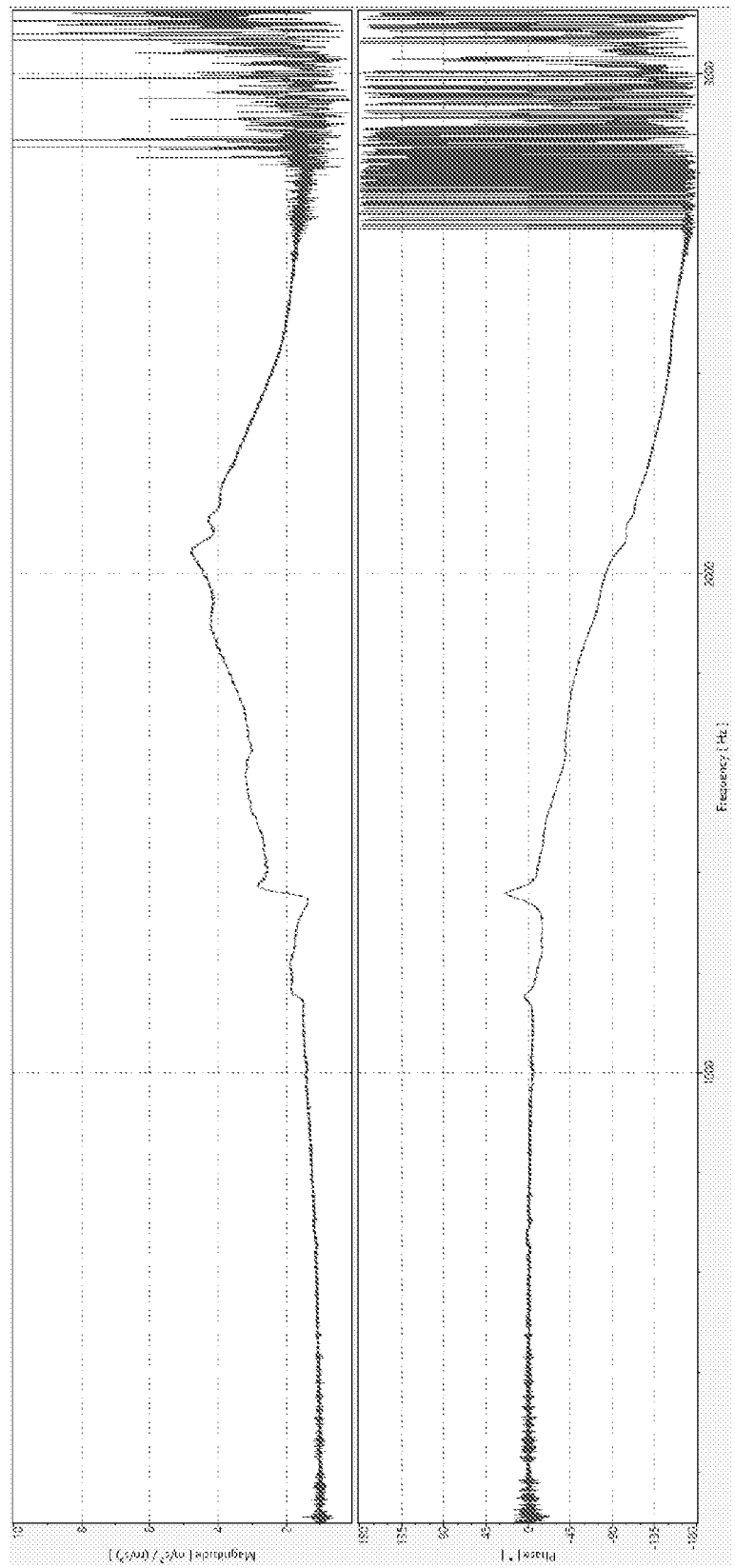

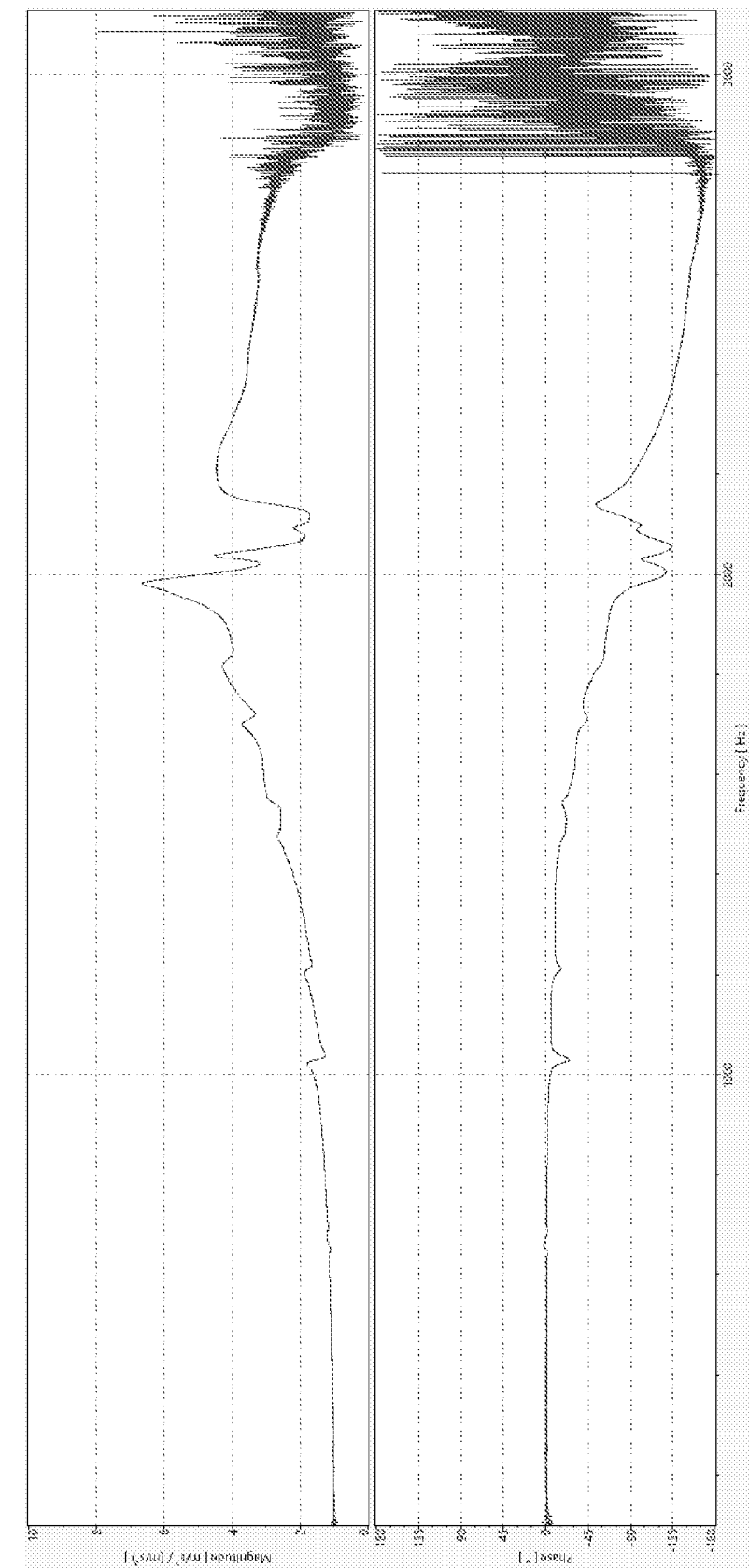

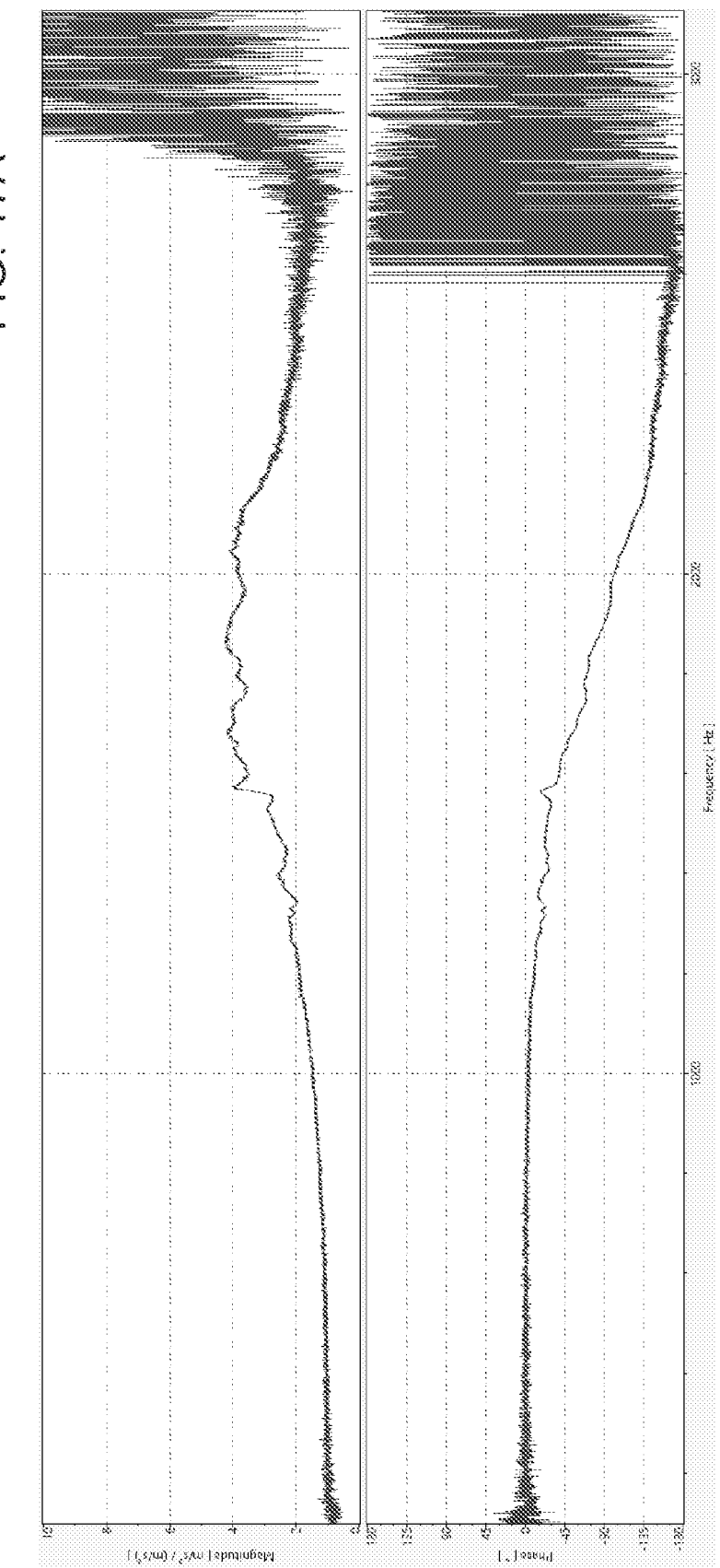

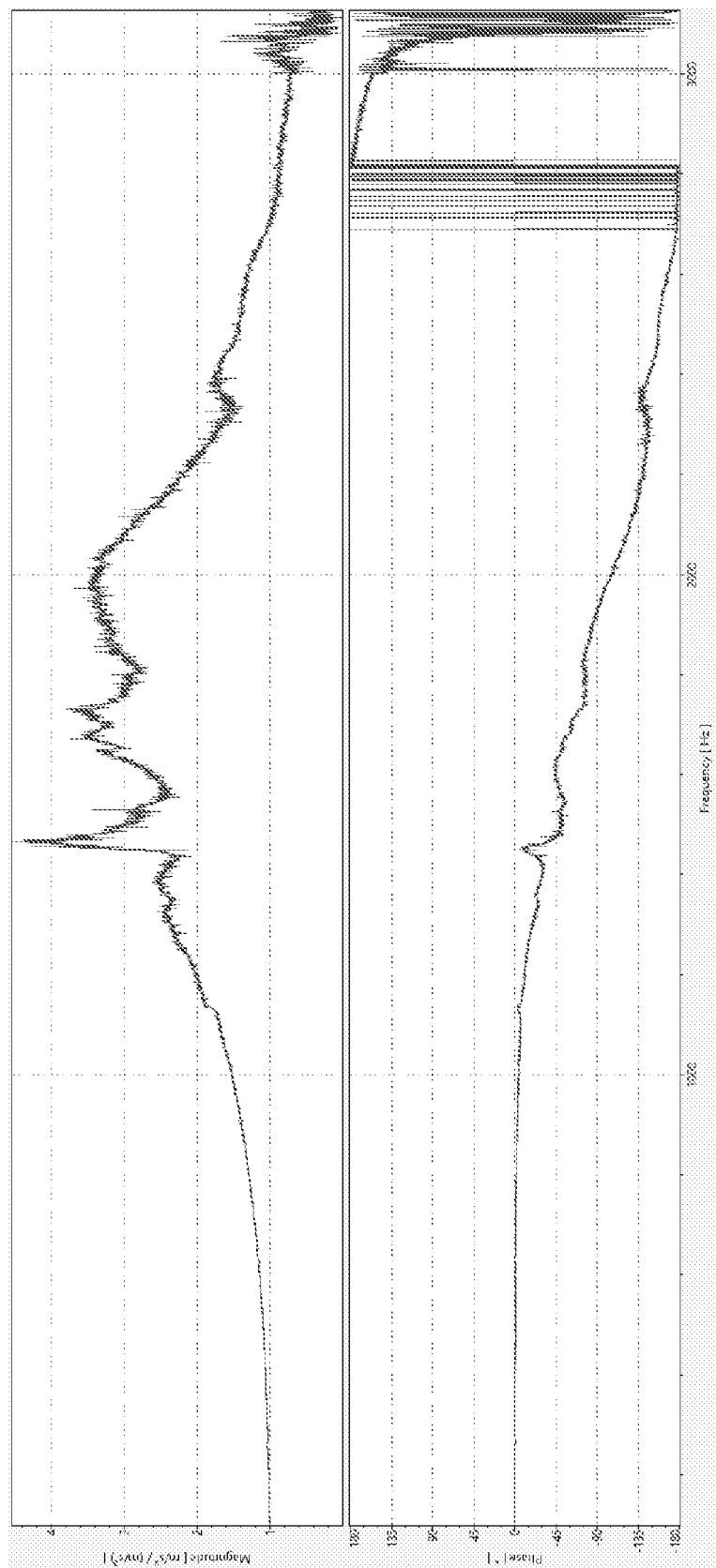

IMPLANTABLE MEDICAL DEVICE WITH RELATIVE MOTION CONTROL

CROSS REFERENCE TO RELATED APPLICATIONS

This application claims the benefit of and priority to U.S. Provisional Patent Application Ser. No. 63/065,277 filed on Aug. 13, 2020, the disclosure of which is incorporated herein by reference.

BACKGROUND

Implantable medical devices are commonly used today to monitor physiological or other parameters of a patient and/or deliver therapy to a patient. For example, various medical devices (e.g., neural stimulators, pacemakers, defibrillators, cardiac monitors, drug pumps etc.) can be implanted in a patient's body to monitor and/or treat heart and/or nervous system related conditions. Some such devices may monitor and, in some cases, provide electrical therapy (e.g. pacing, defibrillation, neuromodulation, etc.) or other therapy (drug or insulin pumps) to the body. Relative motion between the electrical circuitry and other components within the device may lead to interconnect problems and/or other failures. In some cases, there may be a desire to reduce relative motion within the implantable medical device to increase device reliability.

SUMMARY

This disclosure provides design, material, and use alternatives for medical devices, including delivery systems.

In an example, an implantable medical device comprises operational circuitry for the implantable medical device including a first plurality of electrical components, a metal canister shaped for housing the operational circuitry, and a dampening layer selectively disposed over and attached to the first plurality of electrical components, the dampening layer providing electrical isolation to the first plurality of electrical components and configured to reduce susceptibility to vibration of the first plurality of electrical components.

Alternatively or additionally to the above example, the dampening layer is in direct contact with the canister.

Alternatively or additionally to any of the above examples, the dampening layer is molded onto the first plurality of electrical components.

Alternatively or additionally to any of the above examples, the dampening layer comprises a thermoplastic, an elastomer, or a thermoplastic elastomer.

Alternatively or additionally to any of the above examples, the dampening layer omits epoxy.

Alternatively or additionally to any of the above examples, the dampening layer is a hot melt polymer configured to be molded under low pressure.

Alternatively or additionally to any of the above examples, the dampening layer is impregnated with a desiccant.

Alternatively or additionally to any of the above examples, the dampening layer is impregnated with a hydrogen getter material.

Alternatively or additionally to any of the above examples, the dampening layer provides a positive fixation of the operational circuitry to the canister by adhesion to the canister.

Alternatively or additionally to any of the above examples, the dampening layer provides mechanical fixation of the operational circuitry to the canister.

Alternatively or additionally to any of the above examples, the dampening layer forms one or more cavities containing a desiccant and/or hydrogen getter material.

Alternatively or additionally to any of the above examples, the dampening layer forms one or more cavities containing an X-Ray identification marker.

Alternatively or additionally to any of the above examples, the operational circuitry includes a printed circuit board assembly (PCBA), and the dampening layer provides mechanical fixation of one or more of batteries, capacitors, dump shields, speakers, telemetry components, and recharging coils to the PCBA.

Alternatively or additionally to any of the above examples, the dampening layer is impregnated with an activated carbon or charcoal to absorb certain organic and/or inorganic compounds from surfaces of the operational circuitry.

Alternatively or additionally to any of the above examples, the dampening layer is impregnated with a composite desiccant selected to achieve pre-determined moisture uptake properties.

Alternatively or additionally to any of the above examples, the dampening layer is a composite including two or more polymeric materials.

Alternatively or additionally to any of the above examples, the operational circuitry includes at least one second electrical component, and the dampening layer is not disposed over to the at least one second electrical component.

Alternatively or additionally to any of the above examples, the at least one second electrical component includes at least one of a battery, an accelerometer, a piezo speaker, an analog timing crystal, and a Bluetooth module.

Alternatively or additionally to any of the above examples, the dampening layer includes a plurality of projections configured to provide an interference fit with the inner surface of the canister.

Alternatively or additionally to any of the above examples, the medical device is devoid of any metallic layer between the dampening layer and the canister.

Alternatively or additionally to any of the above examples, the medical device is devoid of any insulating layer between the dampening layer and the canister.

Alternatively or additionally to any of the above examples, the operational circuitry is configured to sense biological activity, and/or to deliver electrical therapy.

In another example, an implantable medical device comprises a canister, a plurality of electrical components connected to form operational circuitry, and a moldable material molded onto the operational circuitry, the moldable material and operational circuitry forming a submodule, the moldable material including a thermoplastic, elastomer, thermoplastic elastomer, or hot melt polymer, wherein the submodule is disposed within the canister, the moldable material provides an adhesive connection or a compression fit with the canister, and the moldable material is configured to reduce internal motion of the operational circuitry.

Alternatively or additionally to any of the above examples, the canister is metal, and the moldable material is in direct contact with an inner surface of the canister.

Alternatively or additionally to any of the above examples, the implantable medical device further comprises at least one additional electrical component within the canister, the moldable material selectively disposed over the operational circuitry but not over the at least one additional electrical component.

Alternatively or additionally to any of the above examples, the moldable material is not an epoxy.

Alternatively or additionally to any of the above examples, the moldable material is a hot melt polymer configured to be molded under low pressure.

Alternatively or additionally to any of the above examples, the moldable material provides a positive fixation of the operational circuitry to the canister by adhesion to the canister.

Alternatively or additionally to any of the above examples, the moldable material provides mechanical fixation of the operational circuitry to the canister.

In another example, a method of manufacturing an implantable medical device, comprises molding a dampening layer onto at least a portion of a printed circuit board assembly (PCBA) having a circuit board carrying a plurality of first electrical components, thereby creating a covered operational circuit, and placing the covered operational circuit into a canister for the medical device, wherein the dampening layer is configured to reduce internal motion of the PCBA and/or components thereon.

Alternatively or additionally to any of the above examples, the PCBA carries at least one second electrical component, and the dampening layer does not cover the at least one second electrical component.

Alternatively or additionally to any of the above examples, the step of molding the dampening layer comprises molding a hot melt polymer configured to be molded under low pressure.

Alternatively or additionally to any of the above examples, the dampening layer provides a positive fixation of the operational circuitry to the canister by adhesion to the canister.

Alternatively or additionally to any of the above examples, the dampening layer provides mechanical fixation of the operational circuitry to the canister.

Alternatively or additionally to any of the above examples, the dampening layer is impregnated with a desiccant.

Alternatively or additionally to any of the above examples, the method further comprises hermetically sealing the canister without the addition of a separate desiccant inside the canister.

Alternatively or additionally to any of the above examples, the dampening layer is impregnated with a hydrogen getter material.

Alternatively or additionally to any of the above examples, the method further comprises hermetically sealing the canister without the addition of a separate getter inside the canister.

Alternatively or additionally to any of the above examples, the moldable material is not an epoxy.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 15A, 15B, 16A, and 16B are graphs of transmissibility magnitude and phase related to frequency at ambient temperature for two different devices illustrating the resonance peaks for each device subject to burst chirp excitation;

FIGS. 17A, 17B, 18A, and 18B are graphs of transmissibility magnitude and phase related to frequency at 40° C. for two different devices illustrating the resonance peaks for each device subject to burst chirp excitation; and FIGS. 19A and 19B are graphs of transmissibility magnitude and phase related to frequency at 40° C. for one device illustrating the resonance peaks for each device subject to burst chirp excitation.

DETAILED DESCRIPTION

Figure 1:
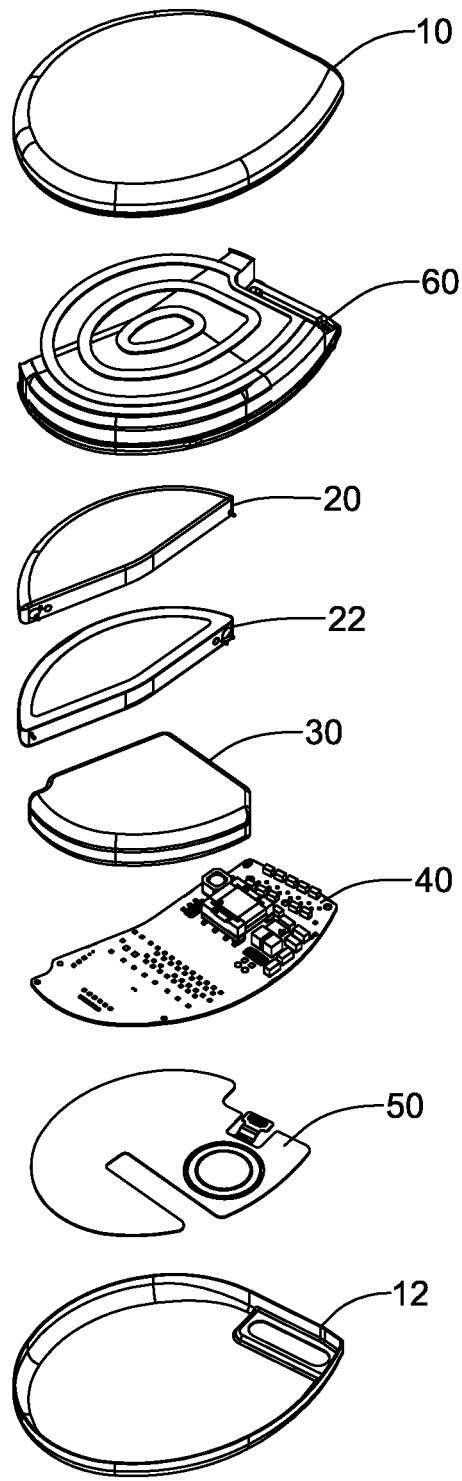
FIG. 1 is an exploded view of an exemplary implantable medical device (IMD)

For the following defined terms, these definitions shall be applied, unless a different definition is given in the claims or elsewhere in this specification. All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

The term "monolithic" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

Many implantable medical devices (defibrillators, pacemakers, monitors, neuro-stimulators or modulators, drug pumps, etc.) comprise a printed circuit board assembly (PCBA), and a battery. The PCBA may typically comprise a circuit board and a plurality of components placed on the circuit board with electrical connections between the components. More than one PCBA may be included, for example an implantable defibrillator may comprise each of high power and low power PCBA builds or "hybrids." The electrical components may include a wide variety of elements, including resistors, capacitors, transistors, discrete logic devices, logic arrays, memory of various types, amplifiers, chips carrying such components (or other components), oscillators, inductors, accelerometers such as in the form of micro-electromechanical systems (MEMS), microcontrollers, etc., without intending limitation to these named items. High power systems such as defibrillators may include specially designed high power capacitors, transformers, and dump resistors.

Pre-molded liners have previously been the primary means of constraining the PCBA relative to the other components within the housing or canister. The canister, which may be conductive, may in some cases be used as an electrode for signal sensing or therapy delivery. The canister is typically hermetically sealed. The hermetically sealed canister typically also contains one or more desiccant elements, for removing residual or encroaching moisture, and a hydrogen getter may be included to capture hydrogen that may be released by device components after hermetic sealing.

Design requirements typically require a variety of validation tests including, for example and without limitation, aging, thermal and mechanical testing, including flex and drop tests, for example. Component variation as well as tolerances amongst components in the canister and on the PCBA can create stresses that may have deleterious effects on, for example, the conductive interconnects between components, and/or on the components themselves, such as relatively sensitive optical isolators (when included). Moreover, relatively larger components, such as batteries and (particularly for defibrillators) high power capacitors have higher mass than other components and may place greater strain on interconnects and PCBA itself. New and alternative approaches to controlling motion and/or vibration in the device are desired.

The innovations described below may be used in conjunction with many types of implantable medical devices (IMD) and/or wearable medical devices. In some examples, the medical device may be, but is not limited to, an implantable cardiac monitor (ICM), an implantable cardioverter-defibrillator (ICD), an implantable pacemaker, leadless cardiac pacemaker (LCP) or other implantable electrophysiology device configured to be implanted in the body, including near or in the heart. Other implantable devices may include neurostimulation devices, such as those for deep brain stimulation, spinal cord stimulation, vagus nerve stimulation, sacral nerve stimulation, and other brain, heart, or peripheral neural stimulation, implantable pumps and/or sensors for use in, for example and without limitation, diabetes management, drug delivery, etc., and any other implantable medical device, particularly active medical devices having electronics therein for one or more of delivering therapy, sensing biological conditions, and/or communicating with other implanted or external devices.

FIG. 1 is an exploded view of an example IMD. The canister as illustrated includes a first canister component 10 and a second canister component 12. The first and second canister components 10, 12 may be made of any suitable biocompatible material. Titanium is an illustrative material, although other materials, such as medical grade stainless steel, may be used in place of or in combination with titanium. Portions of the outside of the first and second canister components 10, 12 may be coated, shaped, or treated in any suitable fashion. In some embodiments, the first and second canister components 10, 12 may be configured to matingly fit together, for example, in a snap fit or an overlapping fit. Typically, the completed device will have a weld seam joining the first canister component 10 to the second canister component 12, although additional intermediate members may also be included on the inside or outside of the device, and welding need not be used for some embodiments using, for example, adhesive or snap-fit.

Internal parts shown in the exploded view include the operational circuitry of the device. In the illustrative embodiment shown, the operational circuitry is shown in a highly simplified fashion, and includes capacitors 20, 22, a battery 30, and PCBA 40. Also illustrated is an electromagnetic interference (EMI) shield 50, which may include a dump resistor as disclosed in U.S. Pat. No. 9,713,725, the disclosure of which is incorporated herein by reference. The operational circuitry shown is for an ICD (having relatively large capacitors 20, 22), but may take a variety of other forms as noted above. The precise details of the components and/or the operational circuitry generally may vary widely depending upon the desired functionality of the device.

The operational circuitry contained within the IMD is highly sensitive, and relative motion between the PCBA and other elements within the canister may result in interconnect issues. In some cases, vibration or device flexure may lead to cracked traces, cracked solder joints, and other failures. In order to prevent relative motion between the PCBA 40 and other internal components, a dampening layer may be molded over the PCBA 40. The dampening layer may be a moldable material 60 such as, but not limited to, a thermoplastic, elastomer, thermoplastic elastomer (TPE), or hot melt polymer. In some examples, the dampening layer may be a composite or blend including two or more polymeric materials.

The moldable material 60 may provide a positive fixation of the operational circuitry to the canister by adhering to the canister. In some example, the moldable material achieves such adhesive fixation in the molding process, where the canister or a part thereof is in the mold fixture and, for example, at least partly defines the mold cavity. The moldable material may also or instead provide mechanical fixation to the canister by friction, interlock, or compression fit with the canister, as for example if the canister or a portion thereof is added after molding is completed. In some examples, the moldable material 60 may provide mechanical fixation to hold components such as one or more batteries, capacitors, dump shields, speakers, telemetry components, and recharging coils in relation to the PCBA. The moldable material 60 also reduces connector relative motion within the IMD and provides electrical isolation of sensitive and/or high voltage components.

In some examples, PCBA 40 may be placed in a mold cavity generally matching the internal geometry of the electronic assembly, and the moldable material is molded over the PCBA at low pressure. By generally matching, the preceding sentence may be understood to mean that a mold cavity may be defined using a more or less flat surface spaced from the PCBA board (as placed in the mold cavity fixture) by an appropriate distance allowing all components on the PCBA to be covered by the mold material. For example, if the maximum height of components on the PCBA is, for example and without limitation, 3 millimeters (mm), the mold design may allow for 5 mm of space between the PCBA board and the mold surface, providing at least 2 mm of moldable material at its thinnest point. The design may use, for example and without limitation, a distance of 0.5 to 10 mm, or more or less, as desired, of spacing between the maximum component height and the mold cavity wall. A thicker molded layer may require more time to cool/solidify, while a thinner molded layer may present manufacturing difficulties if voids occur at the desired temperature and pressure. It is not necessary for the mold to be a flat offset from the PCBA. It can be any geometry and does not have to cover every component.

In some examples, the moldable material 60 is not an epoxy and/or does not require heat curing. For example, the moldable material 60 may exclude or omit epoxy entirely. Other examples may include epoxy for select uses within the IMD, but the material used to cover a plurality of components on the PCBA 40 as "moldable material 60" omits epoxy.

One example of material that may be suitable for moldable material 60 is the thermoplastic elastomer, styrene-ethylene-butylene-styrene (SEBS). Other examples include high performance polyamide (PA) hotmelt adhesives, such as Henkel® Macromelt® 653 and Henkel® Macromelt® 673. These are moldable under low pressure (between 2 and 40 bar), are solvent free, have short cycle time (10-50 seconds), do not require a heat curing process, and adhere to polar plastics such as polyamide, acrylonitrile butadiene styrene (ABS), and polyvinyl chloride (PVC). Henkel® Macromelt® 653 has a Shore A hardness of 77. Henkel® Macromelt® 673 has a Shore A hardness of 90. In some examples, polyamide hotmelt molding can achieve enhanced sealing and improved protection of electrical components as compared to conventional 2-part casting materials (epoxy) or potting resins or silicones. The polyamide hotmelt molding material is a single component material that provides water-tight encapsulation and electrical insulation. Other hotmelts may be used, such as the copolymers Henkel® Technomelt® AS4226, or Henkel® Technomelt® AS8998 (a polyolefin).

Further examples include Dymax® Speedmask® maskants including Dymax® Speedmask® 726-SC and Dymax® Speedmask® 728-G. These moldable acrylated urethanes have a fast cure time (8-10 seconds) under UV or visible light, and have a Shore D hardness of 40-55. Another example of a suitable moldable material is Robnor Resin-Lab® EL227CL, a two-part low viscosity polyurethane resin with a Shore A hardness of 16. Other acrylated urethanes may be used, such as Dymax® Speedmask® 9-7001 or Dymax® Speedmask® 9-20479-B-REV-A. A further example of a moldable material is polycaprolactone.

In some examples, the moldable material 60 is molded over just the PCBA 40, omitting the moldable material 60 over other electrical components such as the battery and/or capacitor. In other examples, the moldable material 60 is molded over the PCBA 40 and at least one additional component of the operational circuitry such as, but not limited to, the battery, high voltage capacitors, and interconnects between the battery, high voltage capacitors, and the PCBA. The moldable material 60, in some examples, covers both high voltage and low voltage circuitry. In some examples the moldable material 60 only covers high voltage circuitry. In still other examples, the moldable material 60 covers only low voltage circuitry.

Additional components of the operational circuitry may include, but are not limited to, capacitors and batteries. In the example illustrated in FIG. 2, the moldable material 60 is disposed over a majority of the PCBA 40 and completely encapsulates the battery but the majority of the capacitors 20, 22 are uncovered. The moldable material 60, once molded, defines a plurality of projections 62 on the outer surface of the moldable material 60. In the example illustrated in FIG. 2, the projections 62 are a series of concentric ridges that extend from the moldable material 60 and onto the outer surface of the capacitor 20 and battery 30. The projections 62 may provide an enhanced friction fit with the inner surface of the canister when the device is assembled. In other examples, the moldable material 60 may encapsulate the capacitors 20, 22. The moldable material 60 dampens any internal motion within the device once assembled. Additionally, the moldable material 60 provides electrical isolation for the components of the PCBA 40, and minimizes the risk of tolerance stack issues. In some examples, the moldable material 60 may minimize or completely eliminate the need for liner and/or insulator components. In some examples, the presence of the moldable material 60 does not result in any visible or tactile changes to the end user, including the surgeon and patient, and the mass increase is minimal.

In this example, the moldable material 60 is in direct contact with the inner surface of the canister, and the IMD is devoid of any intervening layer between the moldable material 60 and the canister. In particular, the device is devoid of any intervening metallic, conducting layer or, in the alternative, insulating dielectric layer, between the moldable material 60 and the canister. In other examples, one or more additional layers or components may be provided, such as an electro-magnetic interference (EMI) shield as disclosed in U.S. Pat. Nos. 7,769,457 and/or 9,713,725, the disclosures of which are incorporated herein by reference. The EMI shield can block or absorb external interference as well as preventing internal arcing events. An EMI shield may wrap around the majority of the inner device electronics and the moldable material, if desired. For example, an EMI shield may have first and second sides, connected at an edge, corresponding to the larger faces of the canister, as shown in the U.S. Pat. Nos. 7,769,457 and 9,713,725 patents. A dump resistor may also be provided, for dumping stored energy on the high power capacitors when needed (such as when a patient having a defibrillator has a non-sustained episode of tachyarrhythmia, in which case the capacitors may charge to a high voltage but therapy is not delivered due to spontaneous termination of the identified arrhythmia). Because a dump resistor may need to dissipate a relatively large amount of energy quickly, a larger area resistor may be used, such as one printed on a flexible circuit and placed outside the moldable material and positioned between the moldable material and the canister. The dump resistor can be integrated into an EMI shield, as shown in U.S. Pat. No. 9,713,725. Some examples, such as lower power therapy devices or monitoring devices may omit a dump resistor and/or EMI shield, if desired. In the example shown, the EMI shield and dump resistor is included at 50 (see FIG. 3).

Figure 2:
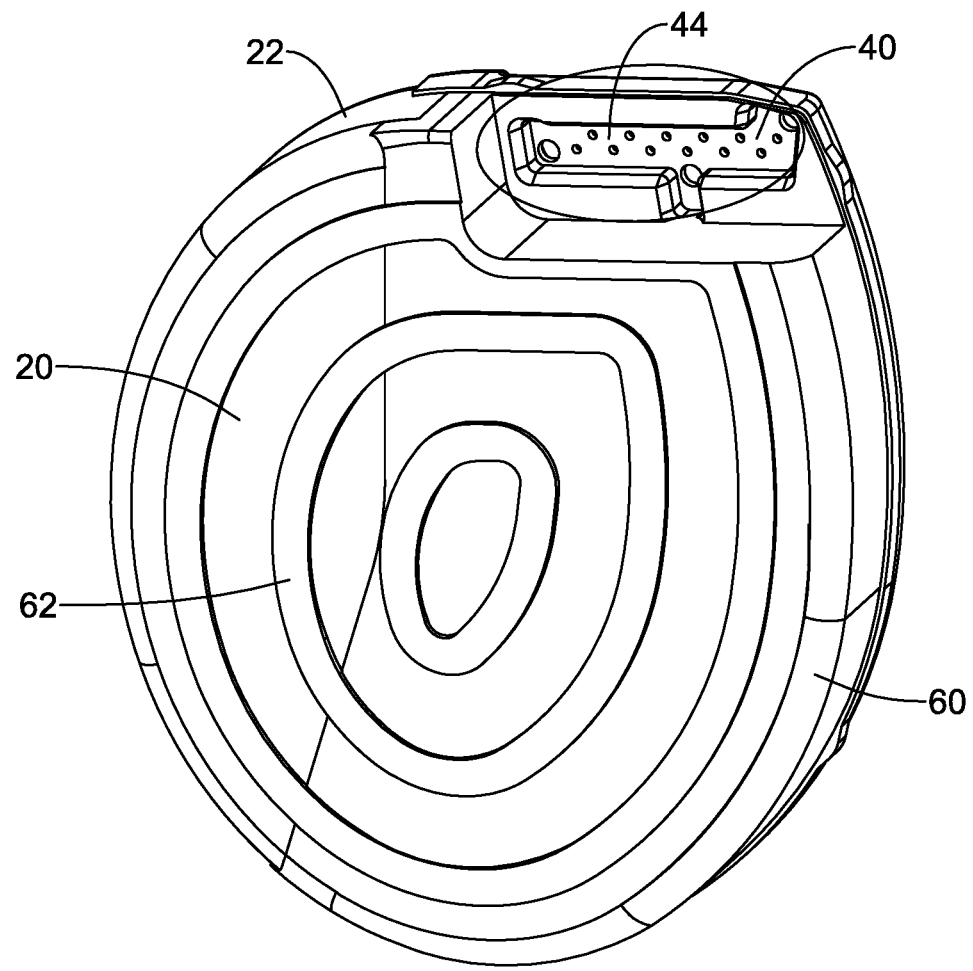
FIG. 2 is front perspective view the IMD of FIG. 1 with the outer cover removed.

FIG. 2 highlights an area at 44 which is configured for coupling to feedthrough pins to a header. As is common in the art, a header is provided in association with a canister for coupling to a lead that attaches mechanically to the header/canister, as well as electrically to the circuitry inside the IMD. For manufacturing purposes, the region of the PCBA that will attach to the feedthrough may be blocked from receiving the moldable material 60. In some examples, certain components of the IMD may be integrated into the header, rather than appearing on the PCBA. For example, an MRI filtering sub circuit may be provided in a header or attached directly to a header, or may be integrated into the feedthrough structure associated with a header. If that is the case, the moldable material 60 may cover internal components but not those associated with the header and feedthrough, if desired.

In an example, the moldable material 60 can be applied over a partial assembly, with the feedthrough wires extending out in the area of the header, and also leaving exposed wires or interconnects for coupling to one or more additional components such as the battery or capacitors. For example, a partial electronic assembly may omit the battery/power source during the application of the moldable material, to avoid stressing the battery cell as well as ensuring that the electronic assembly is not powered and therefore inactive during the molding step. In another example, the moldable material may be added with the aid of a fixture that mates with one half of the canister after the electronic assembly is completed, with battery and header attached, as a final step before the canister is hermetically sealed.

In addition, other components that may be present in the IMD may or may not be covered with the moldable material 60. For example, the anti-motion characteristics of a moldable material 60 may generate a concern about reduced functionality of an accelerometer, or piezo speaker. Such components may be shielded from receiving the moldable layer 60, if desired, during the molding process, or may be omitted from the subassembly during molding with a place for receiving the component shielded from receiving the moldable layer 60 or with an interconnect or wire provided uncovered by the moldable layer 60 after molding. In other example, specific sub-circuits, such as a crystal oscillator, and/or a Bluetooth module may be treated separately and provided without covering from the moldable material.

Some IMD devices have rechargeable batteries (common for neuromodulation systems, for example), and may have associated therewith a charging coil. Other devices may omit a battery and instead rely on received energy, such as magnetic, electrical or mechanical (i.e. sonic or ultrasonic) energy received at a coil or transducer. If desired, the charging coil or other transducer may be provided outside of the moldable material 60, though in some examples the charging coil can be provided such that the moldable material 60 covers it, or it may be provided outside of the canister entirely such as on the side of the canister or in the header. For example, the charging coil may be capable of warming during its operation as it receives incident electrical or magnetic fields from an external device, and this may present a risk of reflow of the moldable material 60.

Figure 3:
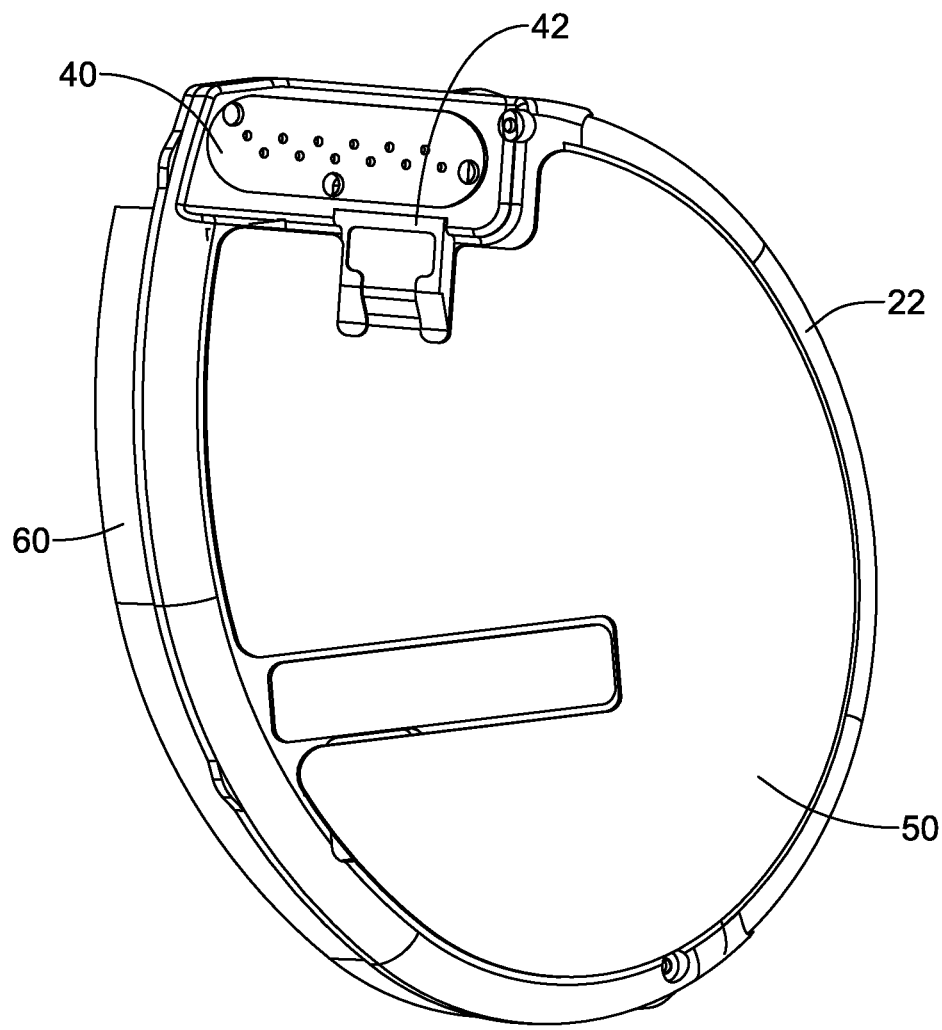
FIG. 3 is a back perspective view of the IMD of FIG. 2.

FIG. 3 illustrates the back of the IMD shown in FIG. 2, showing the moldable material 60 covering the battery, a majority of the PCBA 40, but not the capacitor 22. As shown, the EMI shield 50 and/or dump resistor has been placed over the moldable material 60 and in contact with a portion 42 of the PCBA 40 that is also not covered by the moldable material 60. In another illustration, the EMI shield 50 may also carry a piezoelectric speaker used to issue audible alerts to the user, or a vibrating actuator used to issue a vibration alert to the user. In some examples, items like speakers, vibrating actuators, and some sensors (such as an accelerometer) may be placed outside of the moldable material 60 to prevent the vibration dampening characteristics of the moldable material 60 from impairing functionality of such components.

Figure 4:
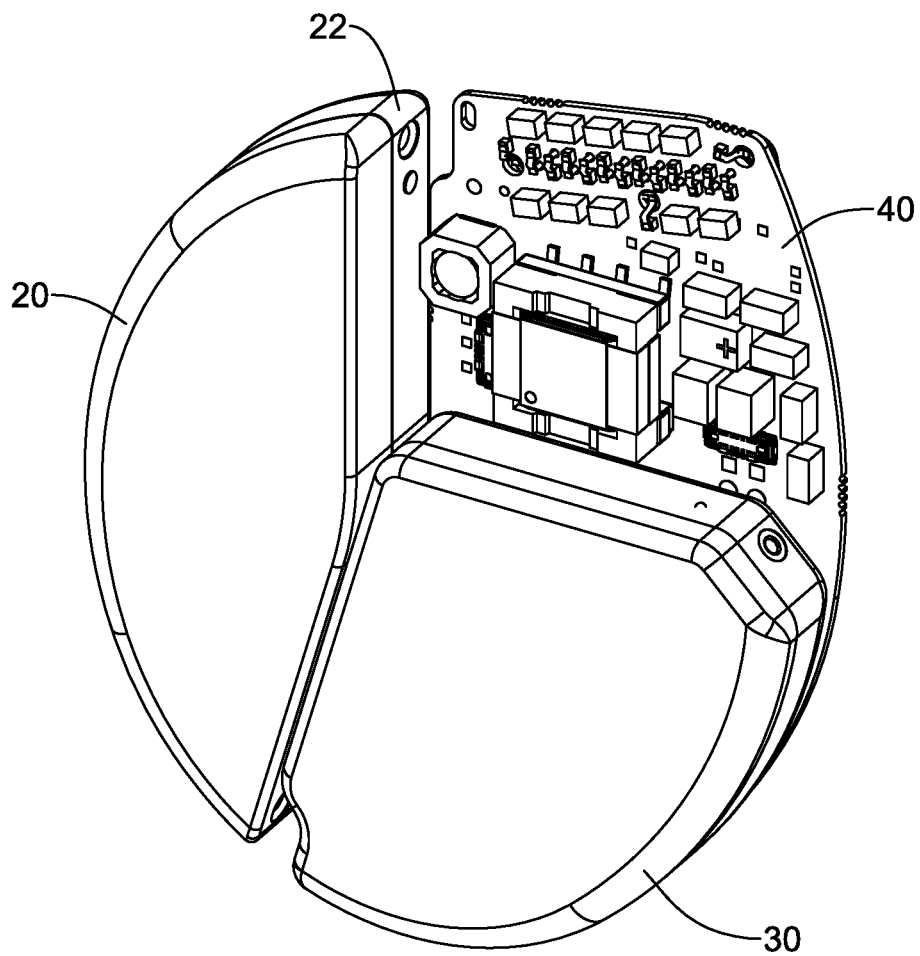
FIG. 4 is a front perspective view of select electronic components before adding the moldable material.
Figure 5:
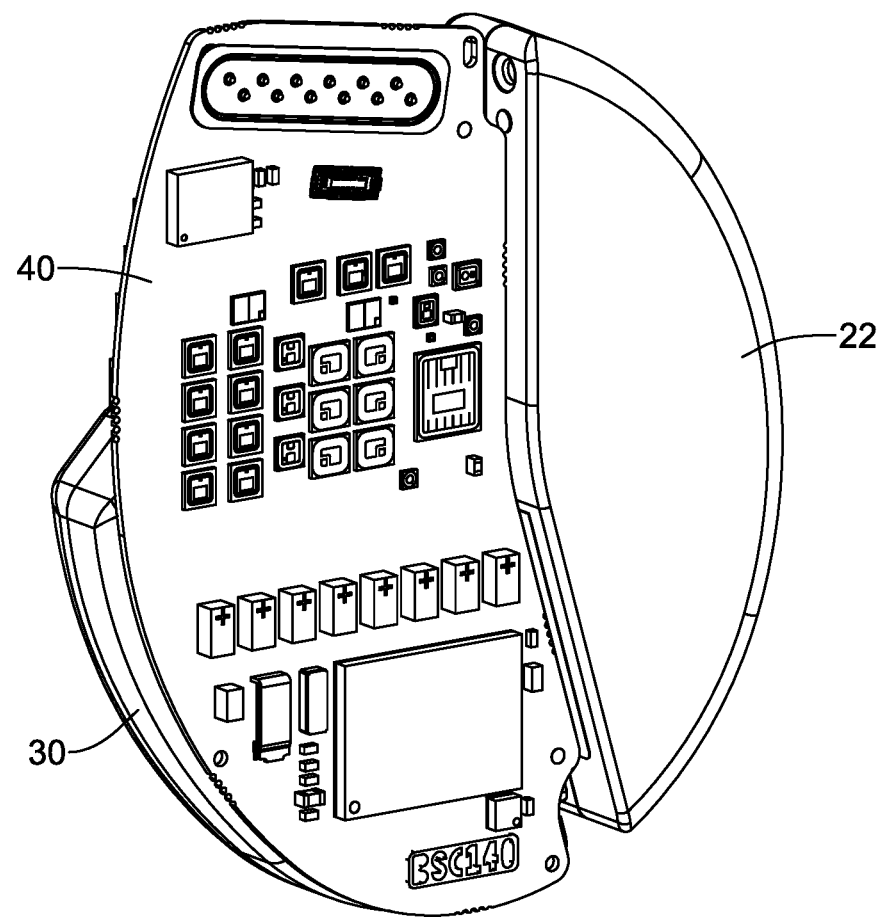
FIG. 5 is a back perspective view of the electronic components of FIG. 4.

FIGS. 4 and 5 show front and back sides, respectively, of an example of the operational circuitry of an IMD before adding the moldable material. The PCBA 40, battery 30, and two (high voltage) capacitors 20, 22 are the parts of the operational circuitry to be at least partly covered with the moldable material. The molding process may be carried out outside of the canister, with the molded assembly inserted into the canister during a later stage of manufacturing. In other examples, the operational circuitry may be disposed in a first part of the canister and the moldable material may be disposed over the circuitry in place, following by welding the second part of the canister to the first part.

A method of manufacturing an IMD using the moldable material begins with selecting the components of the operational circuitry that will be at least partially covered with the moldable material. A mold cavity is then defined by placing a mold cavity, which may be a monolithic part or may have plural pieces that function together, relative to the PCBA and/or other components. The mold itself may also be referred to as a fixture; the mold may include separately moveable parts as for example if a mandrel is provided that can be moved relative to the rest of the mold, with the mandrel used, for example, by pressing it against the PCBA board (or other component) at a location where a void is desired. For example, a mandrel having a hollowed end may be placed over a component that is not to receive the moldable material 60.

Figure 6:
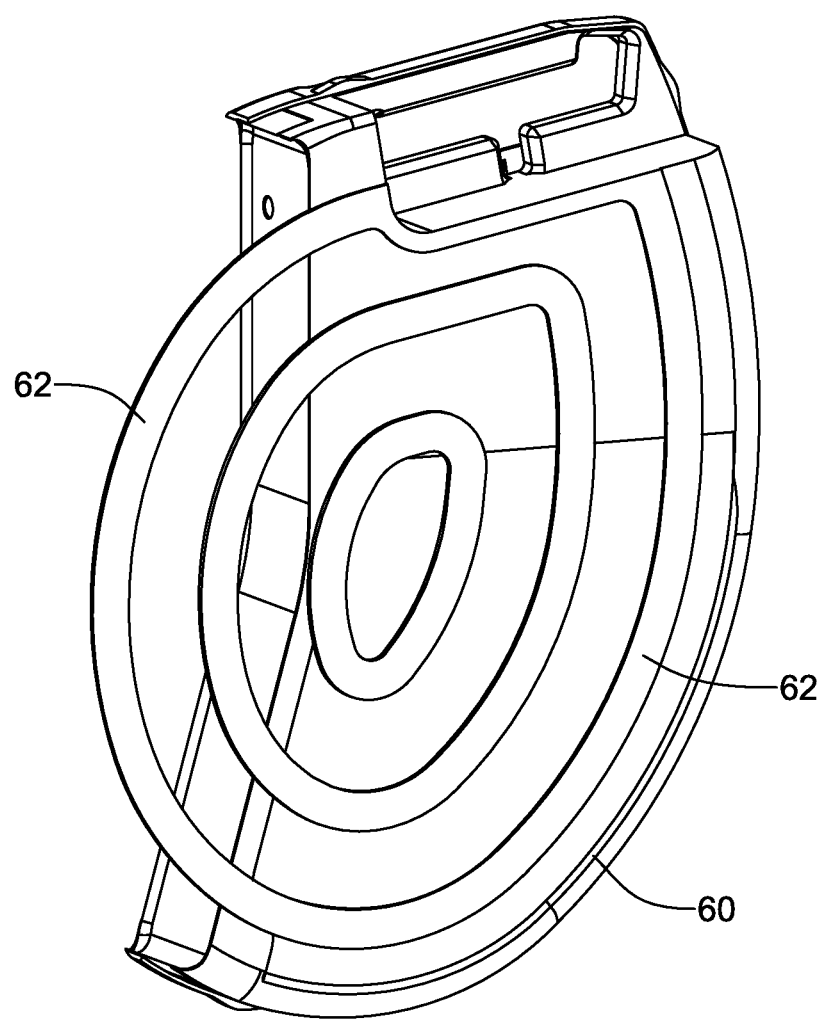
FIGS. 6-9 are front perspective views of different moldable material surface designs.
Figure 7:
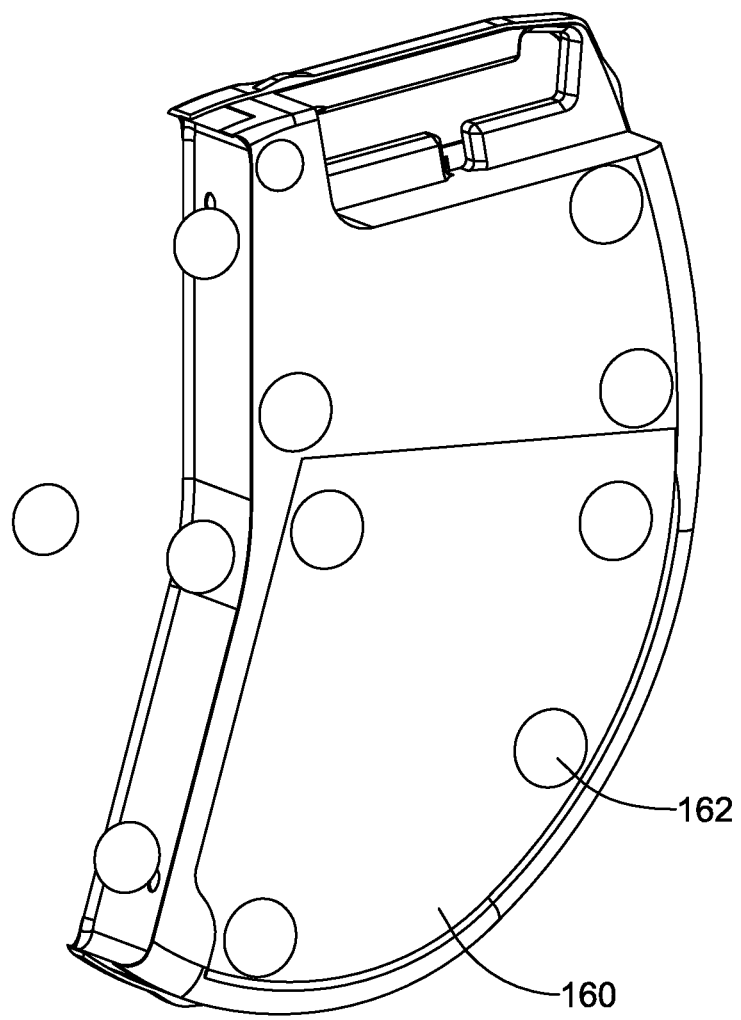
Figure 8:
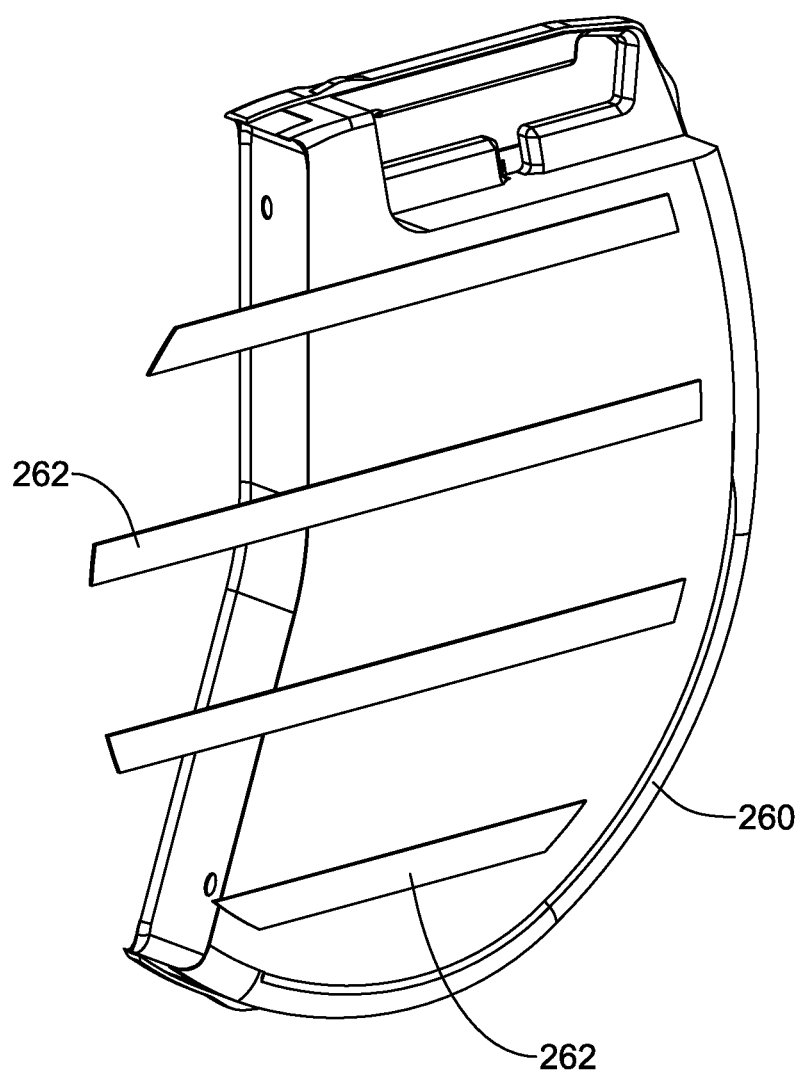
Figure 9:
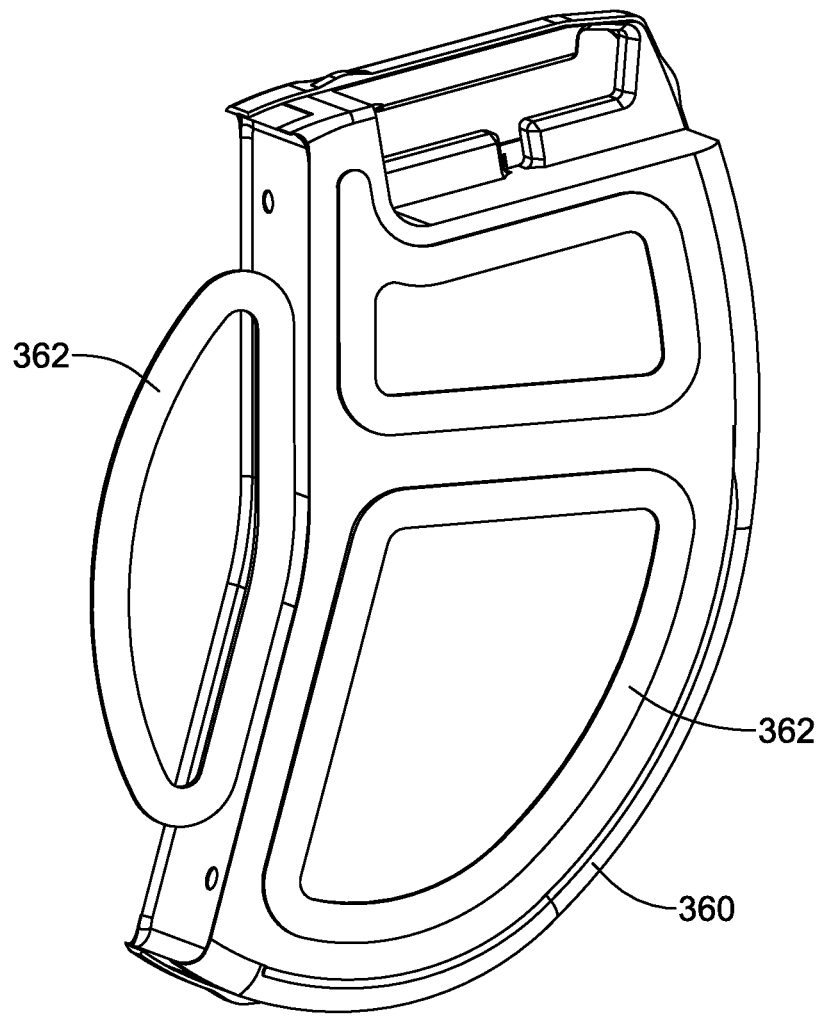

FIGS. 6-9 illustrate various examples of moldable material 60, 160, 260, 360 with different designs for the projection 62, 162, 262, 362. FIG. 6 illustrates the moldable material 60 with projections 62 forming concentric rings that will extend over the capacitor. FIG. 7 illustrates the moldable material 160 with projections 162 forming domes, some of which will be disposed on the capacitor. FIG. 8 illustrates the moldable material 260 with projections 262 forming lines, some of which will extend onto the capacitor. FIG. 9 illustrates the moldable material 360 with projections 362 forming separate outlines, one of which will be disposed on the capacitor. In addition to the projections 62, 162, 262, 362 illustrated in FIGS. 6-9, the projections 62 may include dimples, ribs, wave patterns, or any other structure that provides an interference or friction fit with the inside of the canister. The projections 62 control stack-up, assembly compression force, and/or system vibration response.

Figure 10:
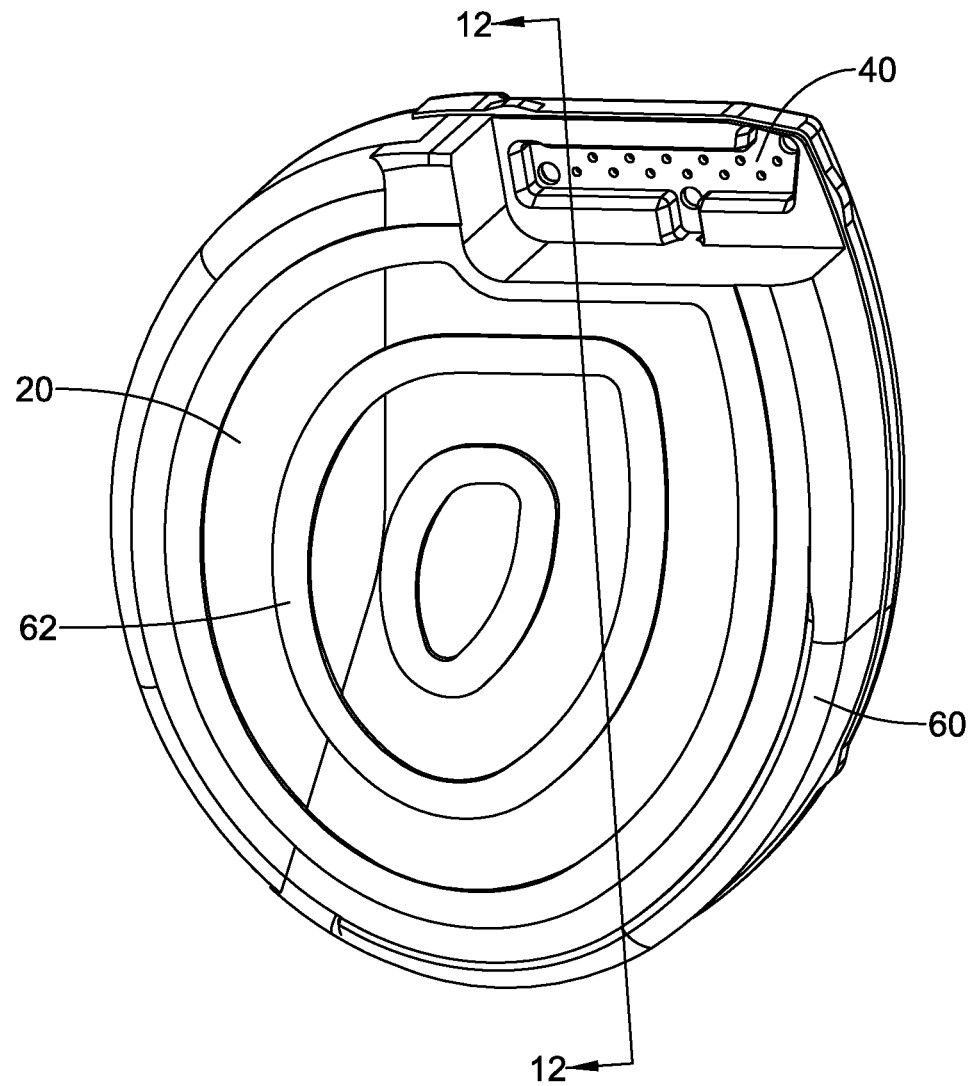
FIG. 10 is a front perspective view of the electronic components of FIG. 4 after adding the moldable material of FIG. 9.
Figure 11:
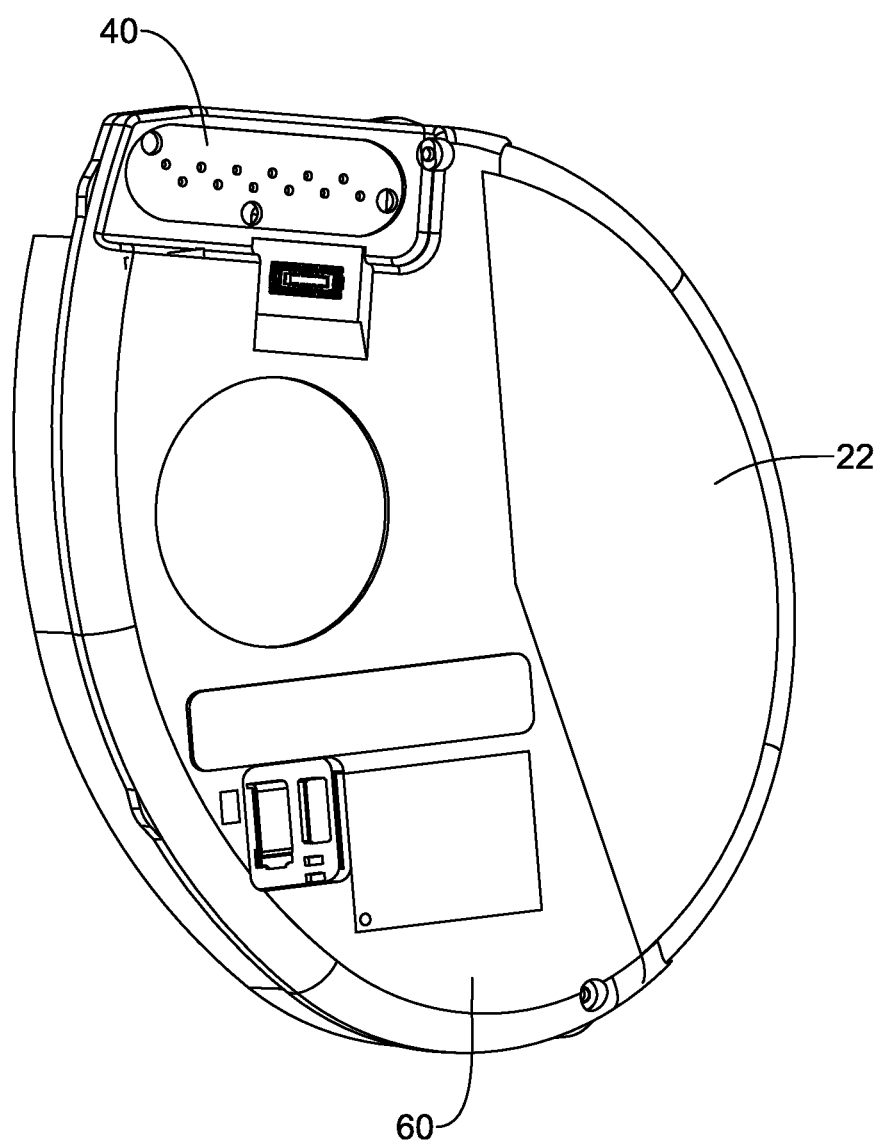
FIG. 11 is a back perspective view of the electronic components of FIG. 5 after adding the moldable material of FIG. 9.
Figure 12:
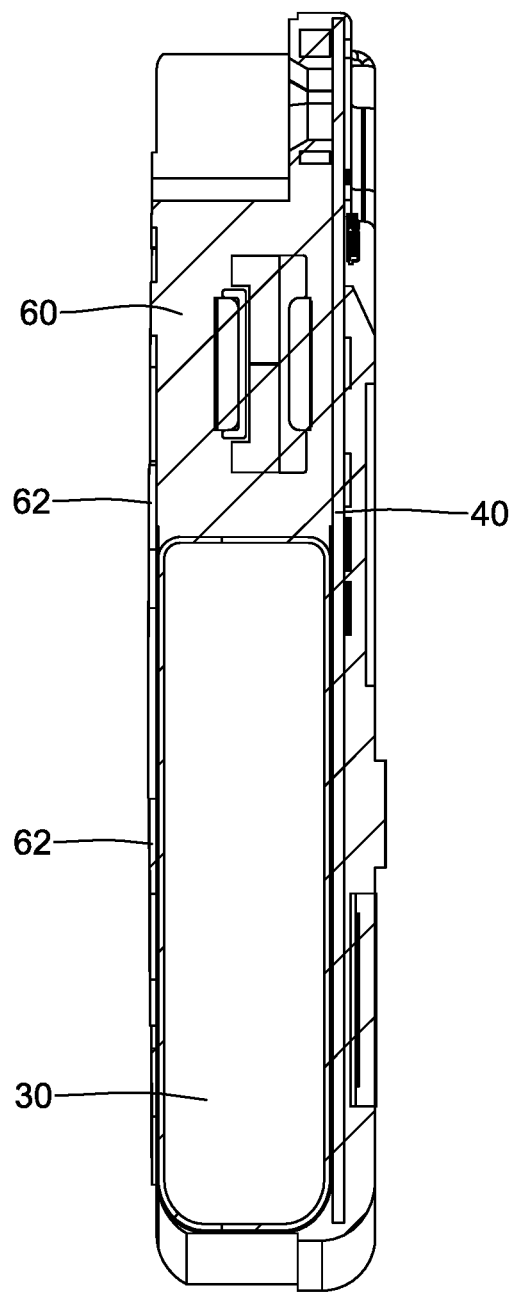
FIG. 12 is a side cross-sectional view taken along line 12-12 in FIG. 10.

In some examples, moldable material 60, 160, 260, 360 will cover the majority of the PCBA 40, the battery will be completely encapsulated, and one of the capacitors 20 will only have projections 62 deposited on the top surface, but otherwise remain uncovered by moldable material 60 as shown in FIG. 10. In some examples of moldable material 60, 160, 260, 360, the second capacitor 22 will generally remain completely uncovered by moldable material 60, as shown in the back view in FIG. 11. On the rear of the device, the moldable material 60 may cover some parts of the PCBA 40 while leaving others uncovered. As shown in the cross-section of FIG. 12, the moldable material 60 may completely encapsulate the battery 30 and a majority of the components on the PCBA 40, with the projections 62 extending above the level of the moldable material 60.

In some examples, intentional voids are left between the encapsulated battery and the canister. This may allow for the battery to swell, as batteries of certain chemistries (such as LiMnO2 and others) often do during use/aging as the chemical reactions inside the battery create changes in thickness. For this reason, in some examples, the moldable material is applied in a mold separate from the canister and then placed in the canister. In other example the battery may not be covered by the moldable material 60.

Figure 13:
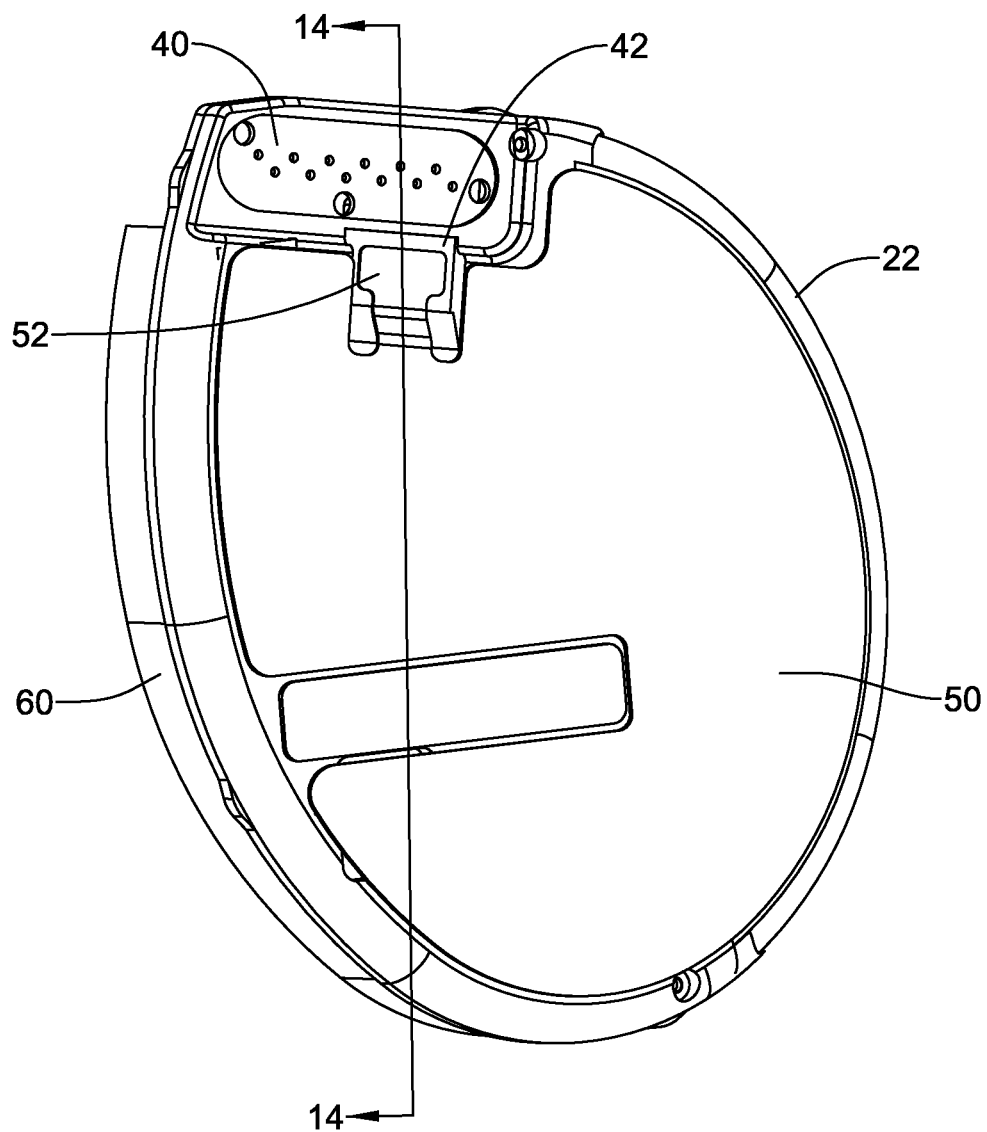
FIG. 13 is a back perspective view of the electronics assembly of FIG. 10 with the capacitors and piezoelectric assembly in place over the moldable material.
Figure 14:
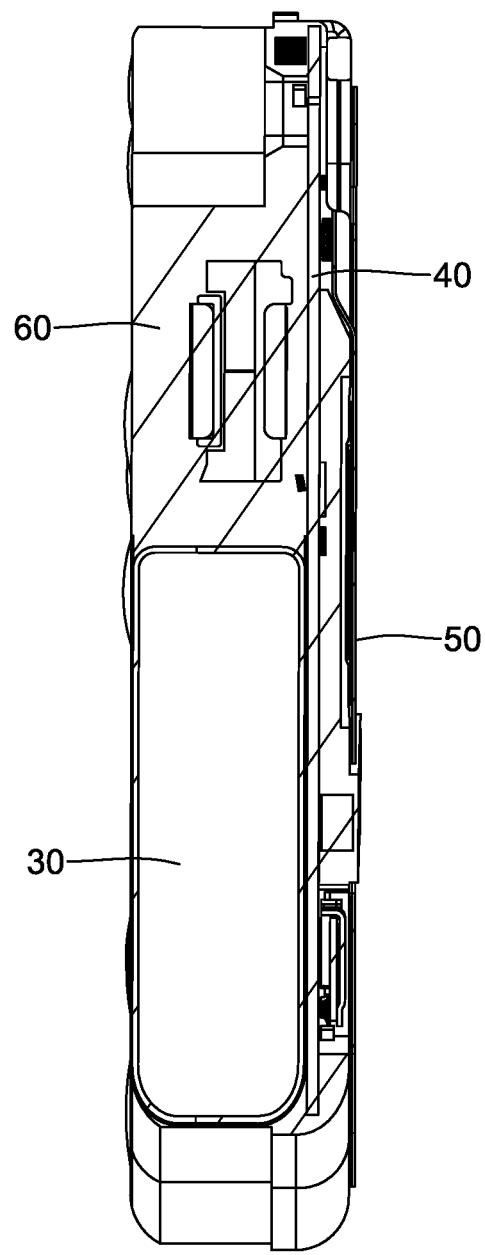
FIG. 14 is a side cross-sectional view taken along line 14-14 in FIG. 13.
Figures 18A, 18B:
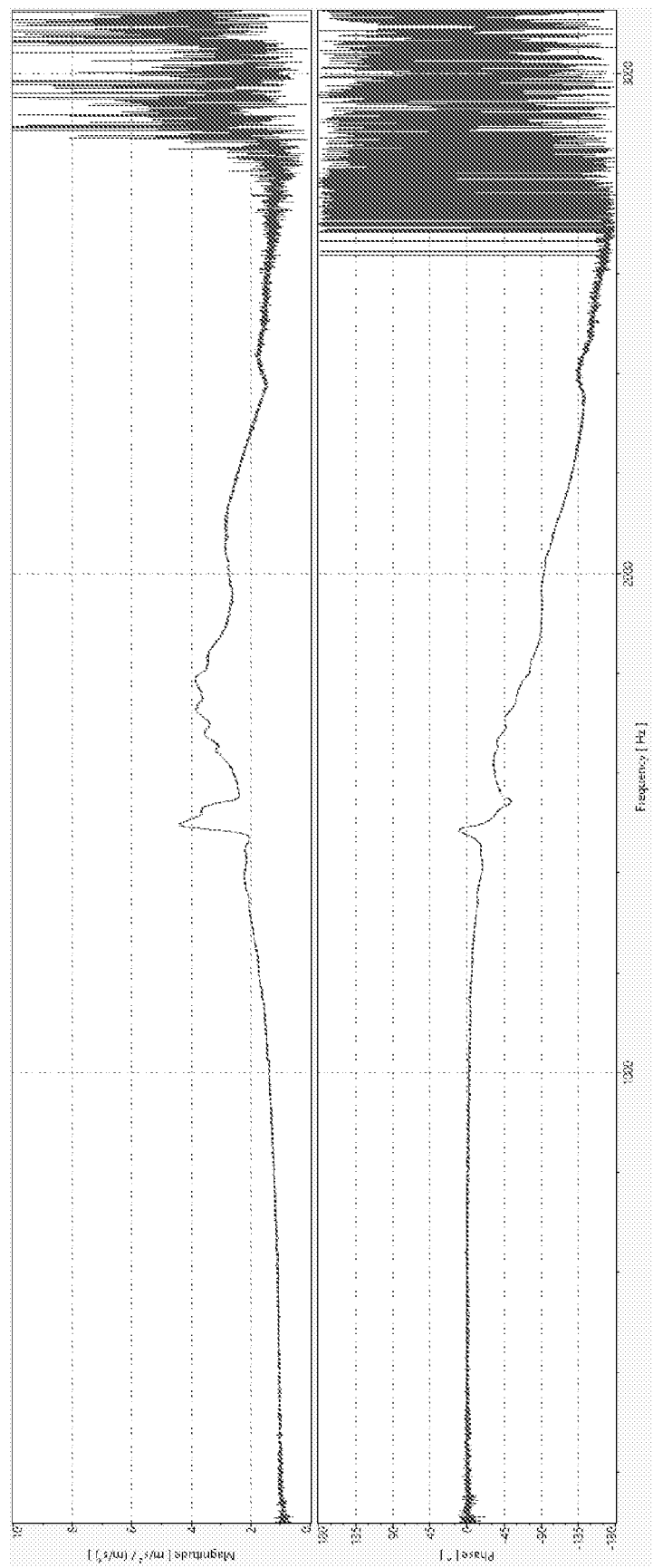

After the moldable material 60 has been molded onto the desired electrical components to form a submodule, the submodule may be assembled with additional components in the canister to form the IMD. As shown in FIGS. 13 and 14, an EMI shield 50 may be added over the moldable material 60 on the back of the device, with a portion 52 of the EMI shield 50 contacting a portion 42 (allowing electrical connection thereto, as the EMI shield 50 may be electrically grounded) of the PCBA 40 remaining uncovered by the moldable material 60.

The method of manufacturing the IMD including the moldable material 60 may be achieved by using the moldable material either to fill large regions or to be selectively placed onto critical locations. The moldable material may be omitted over selected components such as an accelerometer, piezo speaker, analog timing crystal, and Bluetooth module. In one example, the components of operational circuitry to be covered are placed into a mold designed to hold the components and provide an outer shape for the moldable material. The liquefied moldable material is then poured or injected into the mold and allowed to harden. In some examples, the PCBA may have one or more holes to allow the moldable material to flow through, creating internal features that receive desiccant and/or hydrogen getter material.

In one example, the moldable material may form one or more cavities, such as a defined void, for the later placement of desiccant and/or hydrogen getter material. In another example, the moldable material may form a cavity configured to receive an X-Ray identification marker. Post processing, such as a removal process, may be performed to create a cavity or void for placement of a desiccant, hydrogen getter, or X-Ray identification marker. The desiccant, hydrogen getter material, and/or X-Ray identification marker may be added during assembly. In another example, the liquefied moldable material may be selectively deposited onto certain electrical components using a nozzle connected to a reservoir of liquefied moldable material. The projections 62 may be formed either by molding or selective deposition. Elements that are not to be covered with the moldable material may be masked. Examples of masking materials include a polysulfene liner, polymer with a higher melting temperature than the moldable material 60, and/or a metalized shield on a polyetheretherketone (PEEK) liner.

EXAMPLES

Several devices were made, and in some examples, PCBA resonance was eliminated. In other examples, the first resonance frequency of the electronic assembly was changed from about 500 Hz to about 2000 Hz. This change in resonance results in sensitive components being less likely to resonate and be damaged during vibration exposure (such as during shipping, MRI, daily use, etc.). Lower frequencies may be more damaging and more likely to occur, so a higher resonance helps avoid damage and typically indicates a greater level of mechanical robustness. Additionally, selective encapsulation of the moldable material on the electronic assembly exhibits a linear vibration response of the electronic assembly as subject to random vibration as compared to conventional devices which may not. A linear vibration response typically indicates mechanical robustness (i.e. no rattling of components within the housing). A non-linear vibration response may exhibit itself in vibration failure or failure upon exposure to other loading conditions, such as mechanical shock, forces applied by ribs, muscles, and skin when implanted.

The moldable material reduces internal motion of the PCBA relative to other internal components. Laser scanning vibrometer testing may be used to analyze the vibration response of IMDs including moldable material 60 covering one or more internal components. The test examines the magnitude of relative motion at the associated resonance frequencies for moldable material 60 filled devices.

Prior subcutaneous implantable cardioverter defibrillators S-ICD devices built using existing, standard frame and shield techniques were tested to find a resonance frequency of approximately 500 Hz when tested with a 0.3 V burst chirp from 100 to 3000 Hz. Transmissibility is a measure of relative motion that is calculated as the output acceleration divided by the input acceleration of device. A design goal is to reduce the amplitude of the transmissibility, meaning that the internal components are moving similarly to the edge of the pulse generator (PG) can, and also to make the resonance frequency as high as possible.

Two test S-ICD devices were created using functional internal components, but with a moldable material in place of the top liner. The cans were tack welded for closure. These devices were subjected to vibration testing, and FIGS. 15A and 16A show graphs of Magnitude [$m/s^2/(m/s^2)$] on the x axis related to Frequency [Hz] on the y axis, and FIGS. 15B and 16B show graphs of Phase on the x axis related to Frequency [Hz] on the y axis, each using ambient temperature for the testing. Additional testing of the same devices was performed at 40° C. to mimic the device implant environment, as shown in FIGS. 17A-B and 18A-B. There was no PCBA bending mode on these devices; the resonance corresponds with the bending mode of the pulse generator can. The testing did indicate a spike in transmissibility at 1500 Hz, which was determined to be caused by the fixturing itself rather than the device under test. Since the vibration response of the devices with moldable material 60 (Macromelt®) is linear, random vibration testing (14 GRMS) was performed at 40° C. Graphs of results are shown in FIGS. 19A-B. Again, there was no PCBA bending mode, and the observed the resonance corresponds with the bending mode of the pulse generator can.

The inclusion of a moldable material 60, such as the Macromelt® fill improves device vibration performance by increasing the resonance frequency significantly in a burst chirp excitation by eliminating the first bending mode of the PCBA. In these tests, the resonance frequency increased from 430 Hz with prior build processes to 2010 Hz using the moldable material 60. The first PCBA bending mode was eliminated with the addition of the moldable material. The assembly also responded linearly and showed elevated resonance in random vibration excitation. Thus, the testing performed demonstrates the capability of the invention to reduce vibration under the tested conditions, including eliminating the PCBA bending mode.

In some examples, a desiccant may be added to the moldable material when in liquid form and mixed prior to depositing the moldable material onto the selected electronics components. The desiccant may be added in powder or pellet form. Because the moldable material is impregnated with the desiccant, the desiccant provides for a slow uptake of moisture in the first 24 hours, then a rapid uptake after around 48 hours. This slow initial uptake of moisture may allow for the remainder of the assembly steps to be performed out of a glove box, which may reduce manufacturing costs. One example of a desiccant that may be added to the moldable material is a type 3A molecular sieve powder desiccant. Another example is an alkali metal aluminosilicate, the potassium form of the type A crystal structure. Molecular sieves are generally crystalline metal aluminosilicates having a three-dimensional interconnecting network of silica and alumina tetrahedra. Another example of desiccant that may be added to the moldable material includes silica.

In one test, Henkel® Macromelt 653 loaded with desiccant powder was found to saturate after about 72 hours in 27° C. and 65% relative humidity, which is longer than the 24-48 hours for conventional sheet desiccants to become saturated. Adding the desiccant to the polymer extends the saturation time because the polymer slows transmission of the water to the desiccant. The saturation time may depend in part on the permeability of the polymer.

In addition, the typical manufacture would allow for smaller amounts of desiccant to be placed in the device. Blending the desiccant material into the moldable material makes it relatively easy to increase the total amount of desiccant that may be placed. Desiccant uptake for the S-ICD manufactured using prior methods with a sheet desiccant is 60 mg of water vapor. In contrast, manufacturing using the blended moldable material and desiccant allows a larger amount of desiccant to be placed, increasing the total uptake capacity; one test example achieved more than 20% increase (to 73 mg of water vapor). In this example, the desiccant and Macromelt was mixed in a 15:1 ratio. In other examples, the desiccant may be added to the moldable material (whether Macromelt® or other material) in a mix ratio of, for example, 50:1, 40:1, 30:1, 20:1, 10:1, or 5:1.

The liquefied moldable material may also be impregnated with a hydrogen getter material prior to molding. In some examples, both the desiccant and hydrogen getter may be added. In other examples, only one of the desiccant or hydrogen getter may be added to the moldable material. Some examples may use hydrogen getters made of polyisoprene, polybutadiene, polyvinyl propargyl ether, polyacetylene, and polyvinyl acetylene. Use of such getter materials is described in US PG Pub. No. 20150321013, titled IMPLANTABLE MEDICAL DEVICE WITH A HYDROGEN GETTER, the disclosure of which is incorporated herein by reference.

The incorporation of a desiccant and/or hydrogen getter directly into the moldable material may eliminate the need for a separate liner or insulation and/or the placement of separate sheets, dots, gobs, etc. of desiccant and/or getter material. This reduces the steps in manufacturing as well as the overall component count. If additional desiccant and/or hydrogen getter materials are desired, the moldable material may be formed with a cavity to hold the additional materials. In some examples, the manufacturing process may be completed without the addition of a hydrogen getter material other than that provided in the moldable material. In some examples, the manufacturing process may be completed without the addition of a desiccant material other than that provided in the moldable material. Finally, in some examples, the manufacturing process may be completed with both hydrogen getter material and desiccant material omitted except to the extent one, the other, or both are provided in the moldable material.

Incorporation into the moldable material may slow absorption during manufacturing, allowing more of the assembly to take place outside of a glove box. The incorporation of desiccant and/or hydrogen getter directly into the moldable material may also reduce the amount of desiccant and hydrogen getter material needed because there is less air volume in the canister and a reduced moisture envelope due to the volume of moldable material. The elimination of liner and/or insulation may result in a minimal increase in mass gain from the moldable material. Additionally, the molded manufacturing steps may allow for faster and easier design changes, as the moldable material can easily adjust to the addition/subtraction, swapping out, or rearrangement of electronic components.

In some examples, the dampening layer may be impregnated with a composite desiccant that is selected to tailor moisture uptake properties. For example, first and second desiccants having different properties may be used, with a first desiccant that is faster acting and a second desiccant that is slower acing, or other combination. The type and amounts of various desiccants may be selected and combined to achieve specific, pre-determined moisture uptake properties. The composite desiccant may control the uptake rate of moisture as the water vapor levels change inside the canister. For example, the profile of amount of moisture absorbed over various time periods may be achieved with a particular composite of desiccants. For example, silica gel is highly effective at high water vapor levels but poor in low water vapor levels. A molecular sieve is effective at low water vapor levels, but plateaus in its percent moisture uptake as water vapor level increases. Calcium oxide is highly effective in low water vapor levels and has a high capacity uptake when compared to a molecular sieve in a higher water vapor percent environment, but the uptake is very slow. Therefore, the composite mixture achieves a balance between the manufacturing process, design requirement, and long-term capture of moisture generated from potential reactions inside the canister.

In other examples, the dampening layer may be impregnated with an activated carbon or charcoal. As the dampening layer is in direct contact with the PCBA and/or battery, the inclusion of carbon or charcoal may allow the dampening layer to absorb certain organic and/or inorganic compounds, such as sulfur or electrolytes, from surfaces of the operational circuitry (PCBA) and/or battery.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure, and shall not be used to interpret or limit the scope or meaning of the claims.

Various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device comprising:
   operational circuitry for the implantable medical device including a first plurality of electrical components;
   a metal canister shaped for housing the operational circuitry; and
   a dampening layer selectively disposed over and attached to the first plurality of electrical components, the dampening layer providing electrical isolation to the first plurality of electrical components and configured to reduce susceptibility to vibration of the first plurality of electrical components;
   wherein the operational circuitry includes at least one second electrical component, and the dampening layer is not disposed over the at least one second electrical component.

2. The implantable medical device of claim 1, wherein the dampening layer is in direct contact with the canister.

3. An implantable medical device comprising:
   operational circuitry for the implantable medical device including a first plurality of electrical components;
   a metal canister shaped for housing the operational circuitry; and
   a dampening layer selectively disposed over and attached to the first plurality of electrical components, the dampening layer providing electrical isolation to the first plurality of electrical components and configured to reduce susceptibility to vibration of the first plurality of electrical components;
   wherein the dampening layer is molded onto the first plurality of electrical components.

4. The implantable medical device of claim 3, wherein the dampening layer comprises a thermoplastic, an elastomer, or a thermoplastic elastomer.

5. The implantable medical device of claim 3, wherein the dampening layer omits epoxy.

6. The implantable medical device of claim 3, wherein the dampening layer is a hot melt polymer configured to be molded under low pressure.

7. The implantable medical device of claim 3, wherein the dampening layer is impregnated with a desiccant.

8. The implantable medical device of claim 3, wherein the dampening layer is impregnated with a hydrogen getter material.

9. The implantable medical device of claim 3 claim 1, wherein the operational circuitry includes at least one second electrical component, and the dampening layer is not disposed over the at least one second electrical component.

10. The implantable medical device of claim 1 claim 9, wherein the at least one second electrical component includes at least one of a battery, an accelerometer, a piezo speaker, an analog timing crystal, and a Bluetooth module.

11. An implantable medical device comprising:
a canister;
a plurality of electrical components connected to form operational circuitry; and
a moldable material molded onto the operational circuitry, the moldable material and operational circuitry forming a submodule, the moldable material including a thermoplastic, elastomer, thermoplastic elastomer, or hot melt polymer;
wherein the submodule is disposed within the canister, the moldable material provides an adhesive connection or a compression fit with the canister, and the moldable material is configured to reduce internal motion of the operational circuitry.

12. The implantable medical device of claim 11, wherein the canister is metal, and the moldable material is in direct contact with an inner surface of the canister.

13. The implantable medical device of claim 11, further comprising at least one additional electrical component within the canister, the moldable material selectively disposed over the operational circuitry but not over the at least one additional electrical component.

14. The implantable medical device of claim 11, wherein the moldable material is not an epoxy.

15. A method of manufacturing an implantable medical device, comprising:
molding a dampening layer onto at least a portion of a printed circuit board assembly (PCBA) having a circuit board carrying a plurality of first electrical components, thereby creating a covered operational circuit; and
placing the covered operational circuit into a canister for the medical device;
wherein the dampening layer is configured to reduce internal motion of the PCBA and/or components thereon.

16. The method of claim 15, wherein the dampening layer is impregnated with a desiccant.

17. The method of claim 15 further comprising hermetically sealing the canister without the addition of a separate desiccant inside the canister.

18. The method of claim 15, wherein the dampening layer is impregnated with a hydrogen getter material.

19. The method of claim 18 further comprising hermetically sealing the canister without the addition of a separate getter inside the canister.

20. The method of claim 18 wherein the dampening layer is not an epoxy.

* * * * *